United States Patent
Pasternack et al.

(10) Patent No.: US 7,507,571 B2
(45) Date of Patent: Mar. 24, 2009

(54) LISTERIA MONOCYTOGENES BACTERIOPHAGE AND USES THEREOF

(75) Inventors: Gary R. Pasternack, Baltimore, MD (US); Alexander Sulakvelidze, Towson, MD (US)

(73) Assignee: Intralytix, Inc., Baltimore, MD (US)

( * ) Notice: Subject to any disclaimer, the term of this patent is extended or adjusted under 35 U.S.C. 154(b) by 0 days.

(21) Appl. No.: 11/764,587

(22) Filed: Jun. 18, 2007

(65) Prior Publication Data

US 2008/0194000 A1    Aug. 14, 2008

Related U.S. Application Data

(60) Provisional application No. 60/900,794, filed on Feb. 12, 2007.

(51) Int. Cl.
*C12N 7/00* (2006.01)
(52) U.S. Cl. .................................. 435/235.1
(58) Field of Classification Search ........................ None
See application file for complete search history.

(56) References Cited

FOREIGN PATENT DOCUMENTS

| EP | 1 531 692 | 11/2006 |
| WO | WO 2005/059161 | * 6/2005 |

OTHER PUBLICATIONS

Vukov, et al. (2003) "Functional Regulation of the *Listeria monocytogenes* bacteriophage A118 holin by an intragenic inhibitor lacking the first transmembrane domain." Molecular Microbiology 48(1): 173-186.

* cited by examiner

*Primary Examiner*—Bruce Campell
*Assistant Examiner*—Nicole Kinsey White
(74) *Attorney, Agent, or Firm*—Hunton & Williams LLP

(57) ABSTRACT

The present invention is directed to isolated *Listeria monocytogenes* bacteriophage, and methods of using *Listeria monocytogenes* bacteriophage, or polynucleotides and polypeptides derived therefrom, to control the growth or contamination of food products by *Listeria monocytogenes*. The present invention also contemplates the use of *Listeria monocytogenes* bacteriophage, and polynucleotides and polypeptides derived therefrom, for the treatment of host infections or environmental contamination by *Listeria monocytogenes*.

7 Claims, 6 Drawing Sheets

LISTERIA MONOCYTOGENES BACTERIOPHAGE AND USES THEREOF

This application claims benefit of U.S. Provisional Patent Application No. 60/900,794, filed Feb. 12, 2007, the disclosure of which is hereby incorporated by reference.

FIELD OF THE INVENTION

The present invention relates to novel bacteriophage, and compositions corresponding thereto. More specifically, isolated *Listeria monocytogenes* bacteriophage compositions are provided having lytic specificity for *Listeria monocytogenes*, and are useful for controlling growth of *Listeria monocytogenes*, as well as the infection or colonization of food products or food processing equipment by *Listeria monocytogenes*, to control the infection or colonization of processed and unprocessed food products by *Listeria monocytogenes*, or to control the colonization of equipment involved in the processing of the same food product(s). The invention also provides methods of detecting the presence of *Listeria monocytogenes* cells on processed or unprocessed food products, or equipment involved in the processing of the same food products. The invention additionally provides methods of using *Listeria monocytogenes* bacteriophage for the removal of *Listeria monocytogenes* from medical, veterinary, animal husbandry, and other environments where they may be passed to humans or animals. The invention additionally provides for methods of using *Listeria monocytogenes* bacteriophage to treat human diseases caused by *Listeria monocytogenes*.

BACKGROUND OF THE INVENTION

There are six major families of bacteriophages including Myoviridae (T-even bacteriophages), Styloviridae (Lambda bacteriophage groups), Podoviridae (T-7 and related bacteriophage), Microviridae (X174 group), Leviviridae (for example, *E coli* bacteriophage MS2) and Inoviridae as well as coliphages, in general. Other bacteriophage families include members of the Cystoviridae, Microviridae, and Siphoviridae families.

Bacteriophage has been used therapeutically for much of this century. Bacteriophage, which derive their name from the Greek word "phage" meaning "to eat" or "bacteria eaters", were independently discovered by Twort as well as by D'Herelle in the first part of the twentieth century. Early enthusiasm led to the use of bacteriophage as both prophylaxis and therapy for diseases caused by bacteria. However, the results from early studies to evaluate bacteriophage as antimicrobial agents were variable due to the uncontrolled study design and the inability to standardize reagents. Later, in better designed and controlled studies, it was concluded that bacteriophage were not useful as antimicrobial agents (Pyle, N. J., *J. Bacteriol*, 12:245-61 (1936); Colvin, M. G., *J. Infect. Dis.*, 51:17-29 (1932); Boyd et al., *Trans R. Soc. Trop. Med. Hyg.*, 37:243-62 (1944)).

This initial failure of phage as antibacterial agents may have been due to the failure to select for phage that demonstrated high in vitro lytic activity prior to in vivo use. For example, the phage employed may have had little or no activity against the target pathogen, or they may have been used against bacteria that were resistant due to lysogenization or the phage itself may have been lysogenic for the target bacterium (Barrow et al., *Trends in Microbiology*, 5:268-71 (1997)). However, with better understanding of the phage-bacterium interaction and of bacterial virulence factors, it has been possible to conduct studies which demonstrated the in vivo anti-bacterial activity of the bacteriophage (Asheshov et al., *Lancet*, 1:319-20 (1937); Ward, W. E., *J. Infect. Dis.*, 72:172-6 (1943); and Lowbury et al., *J. Gen. Microbiol.*, 9:524-35 (1953)). In the U.S. during the 1940's, Eli Lilly Co. commercially manufactured six phage products for human use, including preparations targeted towards *Staphylococci, Streptococci* and other respiratory pathogens.

With the advent of antibiotics, the therapeutic use of phage gradually fell out of favor in the U.S. and Western Europe, and little subsequent research was conducted. However, in the 1970's and 1980's bacteriophage therapy continued to be utilized in Eastern Europe, most notably in Poland and the former Soviet Union. Alisky et al conducted a review of all Medline citations where bacteriophage was employed therapeutically from 1966 to 1996 (Alisky et al., *J. Infect.*, 36:5-15 (1998)).

There are also several British studies describing controlled trials of bacteriophage raised against specific pathogens in experimentally infected animal models such as mice and guinea pigs (see, e.g., Smith, H. W. & M. B. Huggins, *J. Gen. Microbiol.* 128:307-318 (1982); Smith, H. W. & M. B. Huggins, *J. Gen. Microbiol,* 129:2659-2675 (1983); Smith, H. W. & R. B. Huggins, *J. Gen. Microbiol.*, 133:1111-1126 (1987); Smith, H. W. et al., *J. Gen. Microbiol.*, 133:1127-1135 (1987)). These trials measured objective criteria such as survival rates. Efficacy against *Staphylococcus, Pseudomonas* and *Acinetobacter* infections were observed. These studies are described in more detail below.

One such study concentrated on improving bioavailability of phage in live animals by modifying the bacteriophage (Merril, C. R. et al., *Proc. Natl. Acad. Sci. USA,* 93:3188-3192 (1996)). Reports from the U.S. relating to bacteriophage administration for diagnostic purposes have indicated phage have been safely administered to humans to monitor humoral immune response in adenosine deaminase deficient patients (Ochs et al., *Blood*, 80:1163-71 (1992)) and for analyzing the importance of cell-associated molecules in modulating the immune response in humans (Ochs et al., *Clin. Immunol. Immunopathol.*, 67:S33-40 (1993)).

Additionally, Polish, Georgian and Russian papers describe experiments where phage was administered systemically, topically or orally to treat a wide variety of antimicrobial resistant pathogens (see, e.g., Shabalova, I. A. et al., Abstr. 443. In Proccedings of IX International Cystic Fibrosis Congress, Dublin, Ireland; Slopek S. et al., *Archivum. Immunol. Therapiae Experimental,* 31:267-291 (1983); Slopek, S., et al., *Archivum Immunol. Therapiae Experimental,* 35:569-83 (1987)).

Infections treated with bacteriophage included osteomyelitis, sepsis, empyema, gastroenteritis, suppurative wound infection, pneumonia and dermatitis. Pathogens treated with the bacteriophage include *Staphylococci, Streptococci, Klebsiella, Shigeila, Salmonella, Pseudomonas, Proteus* and *Escherichia*. Articles have reported a range of success rates for phage therapy between 80-95% with only rare reversible allergic or gastrointestinal side effects. These results indicate that bacteriophage may be a useful adjunct in the fight against bacterial diseases.

Despite the use of bacteriophage for the treatment of diseases in humans, there remains in the art a need for the discovery of novel bacteriophage and methods for using these bacteriophage in several critical areas. One significant need concerns the treatment of processed or unprocessed food products to treat or prevent colonization with undesirable pathogens such as *Listeria monocytogenes* which is responsible for food-borne illness. A second critical area of need concerns the removal of undesirable bacteria from industrial environments such as food processing facilities to prevent colonization thereof. A third critical area of need concerns the removal of undesirable pathogens such as *L. monocytogenes* from environments where they may be passed to susceptible humans and animals, such as supermarkets, hospitals, nursing homes, veterinary facilities, and other such environments. Finally, new bacteriophage and methods of using the same are needed for the treatment of human bacterial disease.

SUMMARY OF THE INVENTION

The invention meets those needs and more by providing compositions comprising novel *Listeria monocytogenes* bacteriophage having lytic specificity for *Listeria monocytogenes*. The invention additionally provides methods of using *Listeria monocytogenes* bacteriophage, to control or prevent the infection or colonization of processed and unprocessed food products by *Listeria monocytogenes*, or colonization of equipment involved in the processing of the same food product(s). The invention also provides methods of detecting the presence of *Listeria monocytogenes* cells on processed or unprocessed food products, or equipment involved in the processing of the same food products. The invention additionally provides methods of using *Listeria monocytogenes* bacteriophage for the removal of antibiotic-resistant or other undesirable pathogens from medical, veterinary, animal husbandry, and other environments where they may be passed to humans or animals. The invention additionally provides for methods of using *Listeria monocytogenes* bacteriophage to treat human and/or other animal diseases caused by *Listeria monocytogenes*.

Additional features and advantages of the present invention are described in, and will be apparent from, the following Detailed Description of the Invention and the figures.

DETAILED DESCRIPTION OF THE INVENTION

Definitions

Figure 1A:
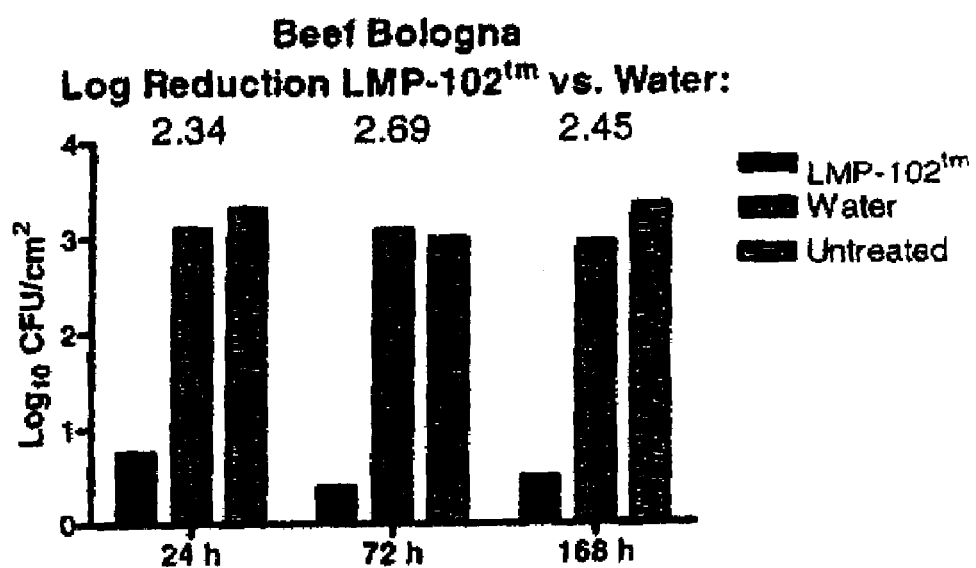
FIGS. 1A-1L show the efficacy of *Listeria monocytogenes* bacteriophage in reducing colonization of ready-to-eat meal and poultry products by *L. monocytogenes*.

As used herein, "isolated" will mean material removed from its original environment (e.g., the natural environment in which the material occurs), and thus is "altered by the hand of man" from its natural environment. Isolated material may be, for example, foreign nucleic acid included in a vector system, foreign nucleic acid contained within a host cell, or any material which has been removed from its original environment and thus altered by the hand of man. Isolated material further encompasses isolated *Listeria monocytogenes* bacteriophage or particular *Listeria monocytogenes* bacterial isolates, isolated and cultured separately from the environment in which it was located, where these isolates are present in purified compositions that do not contain any significant amount of other bacteriophage or bacterial strains, respectively.

As used herein, "significant" will mean an amount of a substance present in the total measured composition, wherein the substance is present in greater than 1% of the total volume or concentration of the composition.

As used herein, "colonization" or "colonized" will refer to the presence of *Listeria monocytogenes* on a foodstuff or environmental surface without perceptible significant alteration to that foodstuff or surface other than the presence of bacteria. The terms "colonization" and "colonized" stand in contrast to the terms "infection" or "infected" which are commonly understood to require perceptible deleterious alteration as part of their definition. "Colonization" and "colonized" may also refer to the presence of bacteria in or on a human or animal without perceptible damage, alteration, or disease.

As used herein, "ATCC" will mean the American Type Culture Collection, located at 10801 University Boulevard, Manassas, Va., 20110-2209, USA.

As used herein, "substantially pure" will mean a macromolecule essentially free of any similar macromolecules that would normally be found with it in nature. In other words, a substantially pure protein is in a composition that contains no more than 5% other proteins from the same taxonomic species. A substantially pure composition excludes media components, excipients or other non-contaminating compounds resulting from culturing, processing or formulating the composition.

As used herein, "amplification" will mean the in vitro production of multiple copies of a particular nucleic acid sequence. The amplified sequence is usually in the form of DNA. A variety of techniques for carrying out such amplification are described in a review article by Van Brunt (1990, *Bio/Technol.*, 8(4):291-294). Polymerase chain reaction or PCR is a prototype of nucleic acid amplification, and use of PCR herein should be considered exemplary of other suitable amplification techniques. Other forms of amplification include, but are not limited to, ligase chain reaction (LCR) and gap-LCR.

*Listeria monocytogenes* Bacteriophage

The invention provides novel *Listeria monocytogenes* bacteriophage particles. In particular, this invention provides isolated *Listeria monocytogenes* bacteriophage List-1, List-2, List-3, List-4, List-36 and List-38, deposited with the ATCC and receiving ATCC Deposit Accession Nos. PTA-5372, PTA-5373, PTA-5374, PTA-5375, PTA-5376 and PTA-5377, respectively. Unless otherwise indicated, use of the term "*Listeria monocytogenes* bacteriophage" in this application is intended to encompass each of the deposited bacteriophage, or mixtures of one or more, up to all of them.

*Listeria monocytogenes* bacteriophage has binding specificity for *Listeria monocytogenes*, and is capable of lysing many infected host *Listeria monocytogenes* cells. Particularly preferred *Listeria monocytogenes* bacteriophage have biological activity (e.g., the ability to lyse host *Listeria monocytogenes* cells and/or the ability to produce phage progeny in a host cell). The invention further contemplates "variants" of *Listeria monocytogenes* bacteriophage, which are bacteriophage having minor variation(s) in the genomic sequence and polypeptides encoded thereby while retaining the same general genotypic and phenotypic characteristics as the *Listeria monocytogenes* bacteriophage. Variants of *Listeria monocytogenes* bacteriophage encompass polymorphic variants. The invention also contemplates "derivative" bacteriophage, which are bacteriophage having modified genotypic or phenotypic characteristics relative to the deposited *Listeria monocytogenes* bacteriophage. Derivative bacteriophage of the invention particularly encompass recombinantly designed *Listeria monocytogenes* bacteriophage harboring genes encoding novel phenotypic traits. Such recombinant *Listeria monocytogenes* bacteriophage are engineered to contain novel genes having traits not found in wild-type *Listeria monocytogenes* bacteriophage. Variant *Listeria monocytogenes* bacteriophage capable of performing the same or equivalent biological functions as *Listeria monocytogenes* bacteriophage are particularly preferred.

The invention contemplates the use of *Listeria monocytogenes* bacteriophage, or variants thereof to control the growth on, or colonization of, processed and unprocessed food products by *Listeria monocytogenes*, or the colonization of buildings and equipment, particularly those associated with the processing of the same food product. The invention also provides methods of detecting the presence of *Listeria monocytogenes* cells on processed or unprocessed food products, or equipment or buildings such as those involved in the processing of the same food products. The invention further provides methods of using *Listeria monocytogenes* bacteriophage for the removal of antibiotic-resistant or other undesirable pathogens from medical, veterinary, animal husbandry, or any additional environments where they may be passed to humans or animals. The invention additionally provides for methods of using *Listeria monocytogenes* bacteriophage to treat human and animal diseases caused by *Listeria monocytogenes*. *Listeria monocytogenes* bacteriophage are administered for the methods of the invention as a homogenous phage administration, or alternatively as a component of a multiphage composition comprising numerous, related bacteriophage, all having lytic specificity for at least one *Listeria monocytogenes* strain. These methods of use are provided with greater particularity infra.

Use of *Listeria monocytogenes* Bacteriophage

Food Preservation

In one embodiment, the invention contemplates a method for the prevention of food borne illnesses caused by the bacterium *Listeria monocytogenes*, comprising contacting a food product or products with a microbial growth inhibiting effective amount of a bacteriophage composition comprising *Listeria monocytogenes* bacteriophage. The modes of contact include, but are not limited to, spraying or misting the *Listeria monocytogenes* bacteriophage composition on the food product(s), or by dipping or soaking the food product(s) in a solution containing a concentration of *Listeria monocytogenes* bacteriophage sufficiently high to inhibit the growth of *Listeria monocytogenes* or adding, injecting or inserting *Listeria monocytogenes* bacteriophage into the food product(s).

In another embodiment, the invention contemplates the application of a *Listeria monocytogenes* bacteriophage composition to equipment associated with the processing of food product(s), such as cutting instruments, conveyor belts, and any other implements utilized in the mass production of food products, including the preparation, storage lad packaging steps of food processing. *Listeria monocytogenes* bacteriophage can additionally be introduced into packaging materials used to contain food product(s), prior to or following transfer of the food product(s) to the packaging materials. Alternatively *Listeria monocytogenes* bacteriophage is useful in the local processing of food products (e.g., in the home or in the restaurant kitchen), using the same modes of contact as described supra.

In another embodiment of the invention, *Listeria monocytogenes* bacteriophage are added as a component of paper products, either during processing or after completion of processing of the paper products. Paper products to which *Listeria monocytogenes* bacteriophage may be added include, but are not limited to, paper towels, toilet paper, moist paper wipes. In a preferred embodiment of the invention, *Listeria monocytogenes* bacteriophage are added as a component of cleansing wipes. *Listeria monocytogenes* bacteriophage may be added in an aqueous state to a liquid-saturated paper product, or alternatively may be added in powder furixi (e.g., lyophilized) to dry paper products, or any combination thereof In similar manner, *Listeria monocytogenes* bacteriophage may be incorporated into films such as those used for packaging foods, e.g., by impregnating or coating the film.

The methods of the invention further contemplate the application of *Listeria monocytogenes* bacteriophage to the floors, walls, ceilings, drains, or other environmental surfaces in structures such as the industrial food processing or home environments. In a particularly preferred embodiment of the invention, *Listeria monocytogenes* bacteriophage is applied to refrigerated devices used to store or transport food or food products, including but not limited to, home and industrial refrigerators, deli meat and cheese counters, refrigerated trucks, and mobile food service vehicles.

In a non-limiting embodiment of the invention, *Listeria monocytogenes* bacteriophage of the invention are useful in preventing the colonization of, or inhibiting the growth of, *Listeria monocytogenes* on processed or unprocessed food products by infecting, lysing or inactivating *Listeria monocytogenes* present on said food product.

Processed or unprocessed food products in which *Listeria monocytogenes* bacteriophage are particularly useful in preventing the growth or colonization of *Listeria monocytogenes* include, but are not limited to, hot dogs, deli meals, luncheon meals, soft cheeses such as feta, brie, camembert, blue-veined cheeses, Mexican-style cheeses, pâtés, meat spreads, smoked seafoods such as salmon, trout, whitefish, cod, tuna or mackerel, poultry, salads, eggs, milk and dairy products, fish, shrimp, frog legs, yeast, coconut, sauces and salad dressing, cake mixes, cream-filled desserts and toppings, dried gelatin, peanut butter, chocolate and ground beef.

*Listeria monocytogenes* bacteriophage can also be administered with ready-to-eat foods and food products such as frankfurters and sliced deli meats including both meat and poultry products as well as whole muscle, sliced, and comminuted products, Additional "ready to eat" foods to which *Listeria monocytogenes* bacteriophage may be administered include, but are not limited to, cooked cured comminuted red meat products (such as beef and pork frankfurters); cooked cured comminuted poultry products (such as turkey frankfurters and chicken bologna); sliced cooked whole red meat muscle cuts, uninjected (such as sliced roast beef and sliced fresh ham prepared from minimally processed cuts); sliced cooked whole poultry muscle cuts, uninjected (such as sliced turkey breast and sliced chicken breast prepared from minimally processed cuts); sliced cooked cured whole red meat muscle cuts (such as corned beef and pastrami); sliced cooked cured whole poultry muscle cuts (such as turkey pastrami); injected whole red meat muscle cuts (such as barn and most processed and/or flavored whole muscle roast beef products); and injected whole poultry muscle cuts (such as most processed and/or flavored whole muscle chicken and turkey breast products.

*Listeria monocytogenes* bacteriophage can also be administered to potable and non-potable water sources to reduce or eliminate the presence of *Listeria monocytogenes*.

*Listeria monocytogenes* bacteriophage compositions of the invention may be provided in aqueous or non-aqueous embodiments for the preservation of food. Aqueous embodiments of *Listeria monocytogenes* bacteriophage include aqueous compositions comprising, or alternatively consisting of, *Listeria monocytogenes* bacteriophage alone or in combination with other bacteriophage. Other bacteriophage include either bacteriophage specific for *Listeria monocytogenes* or bacteriophage specific for other bacterial species, or both.

Aqueous embodiments of *Listeria monocytogenes* bacteriophage are available in solutions that include, but are not limited to, phosphate buffered saline, Luria-Bertani broth or chlorine-free water.

Non-aqueous embodiments of *Listeria monocytogenes* bacteriophage include, but are not limited to, lyophilized compositions or spray-dried compositions comprising, or alternatively consisting of, *Listeria monocytogenes* bacteriophage alone or in combination with other bacteriophage.

*Listeria monocytogenes* bacteriophage can be administered at a concentration effective to inhibit the growth or colonization of food or food products, as well as the equipment used to process or store food. In a non-limiting embodiment of the invention, *Listeria monocytogenes* bacteriophage are typically administered at a growth inhibiting effective amount of a concentration of about $10^7$ to about $10^{11}$ Plaque Forming Units (PFU)/ml, and most preferably at $10^9$ PFU/ml. One of skill in the art is capable of ascertaining bacteriophage concentrations using widely known bacteriophage assay techniques. *Listeria monocytogenes* bacteriophage at such concentrations may be applied at, for example, 1 ml per 500 cm$^2$ of food product.

Environmental Control

In another embodiment of the invention, *Listeria monocytogenes* bacteriophage compositions are administered to environments to control the growth or viability of *Listeria monocytogenes*, particularly the growth or viability of antimicrobial resistant strains of *Listeria monocytogenes*. Antimicrobial resistant *Listeria monocytogenes* include, but are not limited to, *Listeria monocytogenes* showing resistance to ampicillin, amoxicilliniclavulanic acid, chloramphenicol, sulfamethoxazole/trimethoprim, ciprofloxacin, fluoroquinolones, enrofloxacin, clindamycin, penicillin, tetracycline pediocin PA-1, nisin A and cephalosporins. Environments in which *Listeria monocytogenes* bacteriophage is useful to control the growth or viability of *Listeria monocytogenes* include, but are not limited to, medical facilities (including hospitals, out-patient clinics, school and/or university infirmaries, and doctors offices), veterinary offices, animal husbandry facilities, public and private restrooms, and nursing and nursing home facilities. The invention further contemplates the use of *Listeria monocytogenes* bacteriophage for the battlefield decontamination of food stuffs, the environment, and personnel and equipment, both military and non-military.

*Listeria monocytogenes* bacteriophage are additionally useful alone or in combination with other bacteriophage or other compounds, for controlling the growth of biofilms in aquatic environments. Other bacteriophage include either bacteriophage specific for *Listeria monocytogenes* of bacteriophage specific for other bacterial species, or both. Aqueous embodiments of *Listeria monocytogenes* bacteriophage are available in solutions that include, but are not limited to, phosphate buffered saline, Luria-Bertani broth or chlorine-free water. In a particularly preferred embodiment, *Listeria monocytogenes* bacteriophage is used to control biofilm growth in municipal and personal water systems, as well as biofilms present in refrigerated environments.

The modes of administration include, but are not limited to, spraying, hosing, and any other reasonable means of dispersing aqueous or non-aqueous *Listeria monocytogenes* bacteriophage compositions, in an amount sufficiently high to inhibit the growth or viability of *Listeria monocytogenes*. In a non-limiting embodiment of the invention, *Listeria monocytogenes* bacteriophage are useful in preventing the growth or viability of *Listeria monocytogenes* by infecting, lysing or inactivating *Listeria monocytogenes* present in said environment. Administration of the *Listeria monocytogenes* bacteriophage composition includes application to the floors, walls, counter-tops, ceilings, drains or any other environmental surface.

*Listeria monocytogenes* bacteriophage compositions of the invention are available in aqueous or non-aqueous embodiments for the treatment of various environments. Aqueous embodiments of *Listeria monocytogenes* bacteriophage include aqueous compositions comprising, or alternatively consisting of, *Listeria monocytogenes* bacteriophage alone or in combination with other bacteriophage. Aqueous embodiments of *Listeria monocytogenes* bacteriophage are available in solutions that include, but are not limited to, phosphate buffered saline or chlorine-free water.

Non-aqueous embodiments of *Listeria monocytogenes* bacteriophage include, but are not limited to, lyophilized compositions or spray-dried compositions comprising, or alternatively consisting of, *Listeria monocytogenes* bacteriophage alone or in combination with other bacteriophage. Spray-dried compositions may include soluble and/or insoluble carrier materials as processing aids.

In another embodiment of the invention, *Listeria monocytogenes* bacteriophage are added as a component of paper products, either during processing or after completion of processing of the paper products. Paper products to which *Listeria monocytogenes* bacteriophage may be added include, but are not limited to, paper towels, toilet paper and moist paper wipes. In a preferred embodiment of the invention, *Listeria monocytogenes* bacteriophage are added as a component of cleansing wipes. *Listeria monocytogenes* bacteriophage may be added in an aqueous state to a liquid-saturated paper product, or alternatively may be added in powder form (e.g., lyophilized) to dry paper products, or any combination thereof.

*Listeria monocytogenes* bacteriophage can be administered at a concentration effective to inhibit the growth or viability of *Listeria monocytogenes* in a particular environment. In a non-limiting embodiment of the invention, *Listeria monocytogenes* bacteriophage are administered at a concentration of about $10^7$ to $10^{11}$ PFU/ml. One of skill in the art is capable of ascertaining bacteriophage concentrations using widely known bacteriophage assay techniques.

Prevention or Treatment of Infection

In another embodiment, the invention contemplates a method for the prevention or treatment of illnesses caused by the bacterium *Listeria monocytogenes*, comprising contacting a microbial growth inhibiting effective amount of a bacteriophage composition comprising *Listeria monocytogenes* bacteriophage with a site or sites of infection of a host mammal infected with *Listeria monocytogenes*.

The infected mammalian host may be a human host. *Listeria monocytogenes* treatment of infected persons is particularly preferred in the treatment of immuno-compromised persons, pregnant females, and newborns and infants, who are all at an elevated risk of infection by *Listeria monocytogenes*. The modes of contact include, but are not limited to, spraying or misting the *Listeria monocytogenes* bacteriophage composition on the infected mammalian host, by injecting at a site or sites of infection a pharmaceutically acceptable composition containing a concentration of *Listeria monocytogenes* bacteriophage sufficiently high to inhibit the growth of *Listeria monocytogenes*, or by ingesting a solution containing a concentration of *Listeria monocytogenes* bacteriophage sufficiently high to inhibit the growth of *Listeria monocytogenes*.

Additional routes of administration include but are not limited to oral, rectal, topical, ophthalmic, buccal, intravenous, optic, nasal, vaginal, inhalation and intrapleural. The composition is formulated as known in the pharmaceutic arts.

*Listeria monocytogenes* bacteriophage compositions of the invention are available in aqueous or non-aqueous embodiments for the treatment of infection. Aqueous embodiments of *Listeria monocytogenes* bacteriophage include aqueous compositions comprising, or alternatively consisting of, *Listeria monocytogenes* bacteriophage alone or in combination with other bacteriophage. Aqueous embodiments of *Listeria monocytogenes* bacteriophage are available in solutions that include, but are not limited to, phosphate buffered saline or chlorine-free water.

Non-aqueous embodiments of *Listeria monocytogenes* bacteriophage include, but are not limited to, lyophilized compositions or spray-dried compositions comprising, or alternatively consisting of, *Listeria monocytogenes* bacteriophage alone or in combination with other bacteriophage. Spray-dried compositions may include soluble and/or insoluble carrier materials as processing aids.

*Listeria monocytogenes* bacteriophage can be administered at a concentration effective to inhibit the growth or viability of *Listeria monocytogenes* in the infected host. In a non-limiting embodiment of the invention, *Listeria monocytogenes* bacteriophage are administered at a concentration of about $10^7$ to $10^{11}$ PFU/ml. One of skill in the art is capable of ascertaining bacterlophage concentrations using widely known bacteriophage assay techniques.

Depending on the severity of peculiarities of the infection, *Listeria monocytogenes* bacteriophage can be administered to humans (i) orally, in tablet or liquid formulation ($10^5$-$10^{11}$ PFU/dose), (ii) rectally, (iii) locally (skin, eye, ear, nasal mucosa, etc.), in tampons, rinses and creams, (iv) as aerosols or intrapleural injections, (v) intravenously and (vi) intrathecally. Most preferably, bacteriophage can be administered for treatment of *L. monocytogenes* infections by oral or rectal routes.

Production of *Listeria monocytogenes* Bacteriophage

*Listeria monocytogenes* bacteriophage are produced using a culture system. More specifically, host *Listeria monocytogenes* are cultured in batch culture, followed by inoculation of the *Listeria monocytogenes* culture with an appropriate inoculum of *Listeria monocytogenes* bacteriophage. Following incubation, the *Listeria monocytogenes* bacteriophage are harvested and filtered to yield phage progeny suitable for the uses enumerated herein.

The invention provides compositions comprising active viral particles of *Listeria monocytogenes* bacteriophage capable of lysing *Listeria monocytogenes* strains.

The concentration of *Listeria monocytogenes* bacteriophage may be determined using phage titration protocols. The final concentration of *Listeria monocytogenes* bacteriophage can be adjusted by dilution with buffer to yield a phage titer of $10^9$ to $10^{11}$ PFU/ml. The resulting *Listeria monocytogenes* bacteriophage composition can be freeze-dried or spray-dried for storage. On reconstitution, the phage titer can be verified using phage titration protocols and host *Listeria monocytogenes* bacteria. One of skill in the art is capable of determining bacteriophage titers using widely known bacteriophage assay techniques (e.g., Davis et al., "Microbiology" 3$^{rd}$ ed., Harper & Row, Hagerstown, 1980, pp. 874-877, 880-883).

Polynucleotides

Polynucleotides and Variants thereof

The invention contemplates isolated polynucleotide molecules of the *Listeria monocytogenes* bacteriophage, contained within bacteriophage deposits submitted with the ATCC and receiving ATCC Deposit Accession Nos. PTA-5372, PTA-5373, PTA-5374, PTA-5375, PTA-5376 and PTA-5377.

Polynucleotides of the invention encompass polyribonucleotide and polydeoxyribonucleotide, including modified or unmodified RNA or DNA. Polynucleotides of the invention can derive from genomic DNA, as well as cDNA, mRNA and synthetic polynucleotide sequences. One of ordinary skill in the art is well aware of techniques for generating cDNA sequence from mRNA sequence. Polynucleotides of the invention comprise single or double-stranded DNA or RNA sequences, as well as DNA/RNA hybrids.

Polynucleotides of the invention also encompass modified polynucleotides, such as for example phosphorothioated DNAs or PNAs (Peptide Nucleic Acids). Additionally, polynucleotides of the invention may include one or more labels (e.g., radioactive label, biotin, fluorescent label, chemiluminescent or colorimetric label) for diagnostic or tracking and monitoring purposes.

Polynucleotide Fragments

The invention further contemplates fragments of the polynucleotides discussed supra. Polynucleotide fragments are particularly useful for the detection of *Listeria monocytogenes* bacteriophage. Using DNA isolation techniques known in the art or described herein (i.e., CsCl gradients and pulsed field gel electrophoresis), one of skill is capable of using the polynucleotide isolation techniques to obtain *Listeria monocytogenes* bacteriophage DNA, from which polynucleotide fragments are generated. Numerous techniques for generating polynucleotide fragments are also widely known in the art (e.g., restriction digests, pressure-shearing via French Press etc.). Fragments can be isolated via gel electrophoresis or other means and radioactively or non-radioactively labeled for use as probes. DNA fragments can also be purified using HPLC. Labeled polynucleotide fragments are useful under stringent hybridization conditions to identify *Listeria monocytogenes* bacteriophage from a bacteriophage culture or environmental surface. Kits are widely available in the art for labeling polynucleotide fragments (see Invitrogen product catalog and Sigma-Aldrich product catalog).

Polypeptides

Polypeptides and Variants thereof

The invention further encompasses polypeptides encoded by the polynucleotides of the invention, contained within ATCC Deposit Accession Nos. PTA-5372, PTA-5373, PTA-5374, PTA-5375, PTA-5376 and PTA-5377. Polypeptides of the invention may encompass viral coat proteins, transcriptional regulatory proteins and virulence proteins.

Polypeptides of this invention are molecules having an amino acid sequence encoded by polynucleotides of the invention as broadly defined. Polypeptides encompasses proteins, peptides and fragments thereof (functional or non-functional) encoded by *Listeria monocytogenes* bacteriophage polynucleotides. Preferred polypeptides of the invention comprise, or alternatively consist of, antigenic and/or immunogenic polypeptides, especially antigenic and/or immunogenic polypeptide fragments.

Derivative *Listeria monocytogenes* Bacteriophage

Polynucleotides of the invention are also useful for the production of derivative *Listeria monocytogenes* bacteriophage, particularly recombinant *Listeria monocytogenes* bacteriophage. In one embodiment of the invention, homologous recombination techniques are used to introduce homologous sequences encoding alternative proteins, non-functional proteins, or non-coding sequences into the *Listeria monocytogenes* bacteriophage DNA sequence. Such techniques are useful to "knock-out" undesired traits of the *Listeria monocytogenes* bacteriophage, or alternatively to introduce different traits. In a particularly preferred embodiment of the invention, homologous recombination is used to "knock-out" ORFs encoding proteins that are putatively involved in a lysogenic cycle of the *Listeria monocytogenes* bacteriophage.

In another embodiment of the invention, the invention provides recombinant *Listeria monocytogenes* bacteriophage having novel bacteriophage genes introduced into the *Listeria monocytogenes* bacteriophage sequence. In this embodiment, the double-crossover (homologous recombination) method of Loessner et al. (incorporated herein by reference in its entirety) is utilized to introduce a novel bacteriophage gene(s) into the genome of *Listeria monocytogenes* bacteriophage. Successful recombinant *Listeria monocytogenes* bacteriophage replicate in the host *Listeria monocytogenes* cell, producing recombinant progeny phage.

In certain embodiments of the invention it is important to confirm that bacteriophage cocktails contain "lytic" phage rather than "lysogenic" phage, as some lysogenic phage (i.e., transducing phage) may be capable of transferring "undesirable" bacterial genes (e.g., genes encoding bacterial toxins) from one bacterial host to another. Therefore, the use of lysogenic phage on an industrial scale could increase the risk of acquisition of "undesirable" genes from new bacterial strains, which could contribute to the emergence of new pathogenic bacteria. It is therefore prudent to make efforts to avoid or to minimize the use of phage, either in agribusiness or in human therapeutic settings, that (i) contain genes directly associated with bacterial virulence (so that additional virulence genes are not introduced into the environment) and/or (ii) can significantly contribute to the horizontal transfer of virulence-associated genes between bacterial species or strains (to minimize the risk of phage-mediated transduction of undesirable genes). Accordingly, in an alternative embodiment of the invention, homologous recombination is used to "knock-out" undesirable genes such as bacterial toxin genes, or genes having significant homology thereto, found in *Listeria monocytogenes* bacteriophage DNA. A list of undesirable bacterial toxin genes is provided in Table 1. Additional undesirable bacterial genes are listed in 40 CFR § 725.421, which is incorporated herein by reference.

In another embodiment of the invention, homologous recombination is used to introduce or knock-out genes involved in burst size. For example, homologous recombination is used to introduce alternative bacteriophage genes which delay the burst event or increase the phage burst size.

References disclosing alternative bacteriophage genes involved in the timing of the burst event or the size of the phage burst include, but are not limited to, Wang I. N. et al. (2000), *Annu. Rev. Microbiol.;* 54:799-825; and Johnson-Boaz R. et al. (1994), *Mol. Microbiol.,* 13(3):495-504.

Recombinant *Listeria monocytogenes* Bacteriophage Reporter Systems

In another embodiment of the invention, recombinant *Listeria monocytogenes* bacteriophage harboring a reporter system(s) are generated using polynucleotides of the invention. *L. monocytogenes* bacteriophage reporter systems of the invention are useful for the detection of the presence of viable *L. monocytogenes* cells to which the bacteriophage have specificity. Following the technique of Loessner et al., for example, one of skill in the art can generate recombinant *L. monocytogenes* reporter bacteriophage (Loessner et al., *Appl. Environ. Micro.,* 62(4):1133-1140 (1996)). For example, the *Vibrio harveyi* luxAB gene may be introduced into the *L. monocytogenes* bacteriophage DNA sequence using techniques such as homologous recombination. An ideal target for the introduction of the luxAB gene is immediately downstream and in frame with an ORF encoding a *L. monocytogenes* bacteriophage capsid protein, thereby creating a sequence encoding a fusion protein. The preferable location of introduction of the luxAB gene sequence is particularly before any sequence encoding a transcriptional terminator downstream of the ORF encoding a capsid protein. Other *L. monocytogenes* bacteriophage ORF sequences which may function as useful sources of luxAB gene-fusions include gene sequences encoding tail-sheath proteins, or any other late gene region sequences encoding phage head or tail proteins. Such information can be determined using the polynucleotides isolated from ATCC Deposit Accession Nos. PTA-5281, PTA-5284, PTA-5282, PTA-5285, PTA-5283 and PTA-5280 and obtaining and analyzing sequence data derived therefrom. Recombinant polynucleotides harboring the reporter gene are used to generate progeny phage harboring the reporter gene, and expressing the reporter gene-fusion.

TABLE 1

Undesirable (e.g., Bacterial toxin) Genes known to be carried by Transducing Bacteriophages

| Toxin and its Encoding Gene | Bacterial Pathogen | Reference |
| --- | --- | --- |
| Enterotoxin A (entA) | *Staphylococcus aureus* | Betley and Mekalanos, 1988 |
| Enterotoxin A (sea, sel) | *Staphylococcus aureus* | Betley and Mekalanos, 1985 |
| Enterotoxin A (sea) | *Staphylococcus aureus* | Kuroda et al., 2001 |
| Staphylokinase (sak) | *Staphylococcus aureus* | Coleman et al., 1989 |
| Enterotoxin P (sep) | *Staphylococcus aureus* | Kuroda et al., 2001 |
| Exfoliative toxin A (eta) | *Staphylococcus aureus* | Yamaguchi et al., 2000 |
| Diphtheria toxin (tox) | *Corynebacterium diphtheriae* | Freeman, 1951 |
| Shiga toxins (stx1,2) | *Escherichia coli* | O'Brien et al., 1984 |
| Cytotoxin (ctx) | *Pseudomonas aeruginosa* | Nakayama et al., 1999 |
| Cholera toxin (ctxA) | *Vibrio cholerae* | Waldor & Mekalanos, 1996 |
| Cholera toxin (ctxB) | *Vibrio cholerae* | Waldor & Mekalanos, 1996 |
| Zonula occludens toxin (zot) | *Vibrio cholerae* | Koonin, 1992 |
| Neurotoxin (C1) | *Clostridium botulinum* | Barksdale and Arden, 1974. |
| Enterohaemolysin (hly) | *Escherichia coli* | Beutin et al., 1993 |
| Streptococcal exotoxin A (speA) | *Streptococcus pyogenes* | Weeks and Ferretti, 1984 |

TABLE 1-continued

Undesirable (e.g., Bacterial toxin) Genes known to be carried by Transducing Bacteriophages

| Toxin and its Encoding Gene | Bacterial Pathogen | Reference |
| --- | --- | --- |
| Streptococcal exotoxin C (speC) | *Streptococcus pyogenes* | Goshorn and Schlievert, 1989 |
| Streptococcal exotoxin K (speK) | *Streptococcus pyogenes* | Beres et al., 2002 |

Successful recombinant phage are subsequently screened using a luciferase assay in which *L. monocytogenes* bacteriophage (in lysates, for example) containing the luciferase-reporter fusion protein are mixed with a *L. monocytogenes* culture, and cultured for a fixed period of time (e.g., 90 to 120 minutes). Samples are then assayed for bioluminscence using a tube luminometer. Successful recombinant *L. monocytogenes* bacteriophage expressing the reporter fusion protein in the presence of viable *L. monocytogenes* are isolated and cultured to appropriate concentrations to allow for the isolation and storage of said recombinant bacteriophage. The resulting recombinant *L. monocytogenes* bacteriophage may be used with methods of the invention to detect the presence of viable *L. monocytogenes*.

In addition to the Vibrio harveyi luxAB gene, other reporter genes which are useful for the generation of *L. monocytogenes* reporter bacteriophage include, but are not limited to, the firefly luciferase gene.

The invention further contemplates the introduction of one or more of the above-described recombinant events. For example, a recombinant *L. monocytogenes* bacteriophage of the invention may harbor a reporter gene as well as lack a gene associated with the lysogenic cycle.

Use of *Listeria monocytogenes* Bacteriophage Polynucleotides and Polypeptides therefrom Polypeptides such as *Listeria monocytogenes* bacteriophage lytic enzymes encoded by polynucleotides of the invention are used for applications designed to prevent the growth of *Listeria monocytogenes* through cell wall lysis. Thus, lytic polypeptides are useful for the prevention of the growth of *Listeria monocytogenes* on processed and unprocessed food products, as well as equipment used for the processing of said food products.

In another preferred embodiment of the invention, *Listeria monocytogenes* bacteriophage lytic polypeptides are useful for the treatment of one or more infections in a mammal, including humans, by administering a therapeutically effective amount of a *Listeria monocytogenes* bacteriophage lytic enzyme to the patient. This method is useful for the treatment of *Listeria monocytogenes* infections of the gastrointestinal system. Similarly, this method is useful in a prophylactic setting for the prevention of infection by *Listeria monocytogenes* in infant, pregnant or aged mammals, including humans. This method of treatment is further useful for the prevention or other disorders or infections caused by *Listeria monocytogenes*, including but not limited to Listeria meningitis and brain abscesses caused by *Listeria monocytogenes.*

Detection Systems

*Listeria monocytogenes* bacteriophage polynucleotides are particularly preferred in a method of detecting the presence of *Listeria monocytogenes* bacteriophage. For example, fragments of at least 20 nucleotides in length are useful as probes for the identification of the presence of *Listeria monocytogenes* bacteriophage in an environmental or food sample using hybridization techniques. Using stringent hybridization techniques as known in the art, one skilled in the art can determine the presence of *Listeria monocytogenes* bacteriophage in a sample.

In another embodiment of the invention, polynucleotide fragments of between about 16 and about 40 nucleotides in length are useful as primers for the identification of the presence of *Listeria monocytogenes* bacteriophage in, e.g., an environmental or food sample using PCR amplification techniques. These applications are particularly useful in the sense of determining the presence of *Listeria monocytogenes* bacteriophage in food over extended periods of time following treatment of the food with *Listeria monocytogenes* bacteriophage. PCR amplification conditions may vary, but one skilled in the art can readily determine the appropriate PCR amplification conditions (see, e.g., Current Protocols in Molecular Biology, Frederick M. Ausubel et al., ed., Wiley-Interscience, NY, 1989 and periodic updates thereof).

Alternatively, recombinant *Listeria monocytogenes* bacteriophage themselves, such as, for example, the *Listeria monocytogenes* luciferase reporter bacteriophage described supra, are useful in methods of screening food products and food processing equipment for the presence of viable *Listeria monocytogenes*. In such a system, *Listeria monocytogenes* bacteriophage containing a reporter system (such as, for example, a luciferase reporter system) are applied to the sample and analyzed at some time point in the future for the activation of the reporter molecule. The activation of the reporter molecule is indicative of the presence of viable *Listeria monocytogenes* cells.

In a preferred embodiment of the invention, *Listeria monocytogenes* bacteriophage polynucleotides or fragments thereof are useful as probes to detect the presence of *Listeria monocytogenes* bacteriophage. In another embodiment of the invention, *Listeria monocytogenes* bacteriophage polynucleotides or fragments thereof are useful as part of a process for the detection of *Listeria monocytogenes* bacteriophage during production of the same. Alternatively, *Listeria monocytogenes* bacteriophage polynucleotides or fragments thereof are useful for the detection of the presence of *Listeria monocytogenes* bacteriophage introduced into foodstuffs or packaging materials for the same during part of a production method for the production or packaging of food stuffs. In an additional embodiment of the invention, more than one labeled *Listeria monocytogenes* bacteriophage polynucleotide fragment is used as a probe to detect the presence of *Listeria monocytogenes* bacteriophage in a sample. Polynucleotide fragments of the invention useful for the detection of *Listeria monocytogenes* bacteriophage are preferably at least 20 nucleotides in length. Polynucleotide fragments of the invention are also useful for the detection of closely related *Listeria monocytogenes* bacteriophage isolates under stringent or non-stringent hybridization conditions. Polynucleotide fragments of the invention may include one or more labels (e.g., radioactive label, biotin, fluorescent label, chemiluminescent or calorimetric label) for diagnostic or tracking and monitoring purposes.

In another embodiment of the invention, polynucleotides and polypeptides of the invention, or fragments thereof, are used in techniques to identify *Listeria monocytogenes* bacteriophage. By way of the following non-limiting list of experimental techniques, one skilled in the art can easily identify bacteriophage compositions as comprising *Listeria monocytogenes* bacteriophage when the same techniques are performed on a comparative basis against the bacteriophage deposited in ATCC Deposit Accession Nos. PTA-5372, PTA-5373, PTA-5374, PTA-5375, PTA-5376 and PTA-5377. The experimental techniques that can be used include, but are not limited to, DNA sequencing; polymerase chain reaction (PCR) with sequence-specific primers; Southern blot DNA hybridization with sequence-specific nucleic acid probes; restriction fragment length polymorphism (RFLP) analysis; SDS polyacrylamide gel electrophoresis analysis of raw protein extracts; SDS polyacrylamide gel electrophoresis analysis of raw protein extracts with protein sequencing by any means available; peptide mapping experiments; 2D-gel electrophoresis profiles, and Western blot analysis. These and other useful techniques are fully enabled by the deposited bacteriophage in view of the present specification and laboratory references such as "Current Protocols in Molecular Biology," Frederick M. Ausubel et al., ed., Wiley-Interscience, N.Y., 1989 and periodic updates thereof; Sambrook et al., "Molecular Cloning: A Laboratory Manual," 3rd ed., 2001; and Coligan et al., eds., "Current Protocols in Protein Science," Wiley, Brooklyn, N.Y., 2001 and periodic updates thereof, each of which are incorporated herein by reference.

Epidemiological Typing

*Listeria monocytogenes* bacteriophage of the invention are further useful as a tool for the epidemiological typing of *Listeria monocytogenes* isolates. For example, one of skill in the art can use *Listeria monocytogenes* bacteriophage of the invention to screen a panel of *Listeria monocytogenes* isolates to aid in the taxonomic identification of the *Listeria monocytogenes*, by determining which isolates yield a positive lytic reaction to the *Listeria monocytogenes* bacteriophage. (see, for example, Mee-Marquet et al. *Appl. Env. Micro.*, 63(9): 3374-3377 (1997)). *Listeria monocytogenes* bacteriophage can be combined with other *Listeria monocytogenes* specific bacteriophage to further refine the epidemiological typing results. The specificity of the *Listeria monocytogenes* bacteriophage for certain strains of *Listeria monocytogenes* demonstrates the utility of *Listeria monocytogenes* bacteriophage as an epidemiological typing tool.

The invention now will be exemplified in the following non-limiting examples.

EXAMPLES

Example 1

*Listeria monocytogenes* Bacteriophage Isolation

*Listeria monocytogenes* bacteriophage, specifically including LIST-1, LIST-2, LIST-3, LIST-4, LIST-36, and LIST-38, were isolated from Baltimore Inner Harbor waters using lysis of *Listeria monocytogenes* to form plaques in bacterial lawns as a means of detecting the presence of bacteriophage having lytic specificity for *Listeria monocytogenes*. Plaques are harvested, diluted and re-plated on bacterial lawns through a process of serial enrichment until a single bacteriophage species, or monophage, results as determined by a stable restriction fragment length profile of the bacteriophage DNA. The isolates obtained using the technique recited supra may be cultured using the techniques as set forth herein. *Listeria monocytogenes* bacteriophage was deposited with the ATCC, receiving ATCC Deposit Accession Nos. PTA-5372, PTA-5373, PTA-5374, PTA-5375, PTA-5376 and PTA-5377.

PFU concentration of the *Listeria monocytogenes* bacteriophage may be determined using techniques known in the art, such as, for example, the lytic reaction described by Marquet-Van der Mee, N. & A. Audurier, *Appl. Environ. Micro.*, 61(1):303-309 (1995), herein incorporated by reference. Briefly, host *Listeria monocytogenes* cells are inoculated into LB broth (Difco) and incubated at 30° C. until the onset of log phase growth (approximately 3 to 5 hours). Culture plater are then inoculated by flooding of the surface of the Modified Oxford agar (MOX, Difco) or Luria-Bertani broth agar (Difco) with 2 to 3 mls of the broth culture. After removal of the surplus inoculum, the plates are allowed to dry for at least 30 min. at 37° C. The phage preparations are then applied to the seeded agar plates. The plates are incubated overnight at 30° C. The determination of the lytic specificity of *Listeria monocytogenes* bacteriophage for a particular *Listeria monocytogenes* strain is determined by observing the plates for clear plaques on a lawn of bacterial growth.

Example 2

Production of *Listeria monocytogenes* Bacteriophage Lysate in Liquid Culture

*Listeria monocytogenes* Bacteriophage Culturing

Single aliquots of *Listeria monocytogenes*, stored in 70% LB broth/30% glycerol medium, were revived from a −80° C. freezer. The *Listeria monocytogenes* culture was allowed to thaw at room temperature for 15-30 min., followed by brief vortexing. Ten ml of *Listeria monocytogenes* were inoculated into 35 ml of LB-broth medium, and cultured at 30° C. at 150 rpm over-night on a rotary shaker. The resulting $OD_{600}$ of the culture was approximately 0.3-0.4.

Ten ml of *Listeria monocytogenes* were inoculated into 100 ml of LB broth medium, and cultured at 30° C. at 150 rpm for approximately 2-2.5 hours, until the $OD_{600}$ reaches 0.1. To this culture were added a total of approximately $10^9$ PFU of *Listeria monocytogenes* bacteriophage. PFU of the *Listeria monocytogenes* bacteriophage was confirmed before-hand.

The mixture was then transferred to a 2 L flask containing 1.0 L of LB broth. The mixture was cultured at 30° C. at 150 rpm for approximately 5-7 hours, until the $OD_{600}$ reaches 0.04-0.01. At this point, *Listeria monocytogenes* bacteriophage were harvested and purified.

Alternatively phage propagation can be carried out in 1 to 5 L flasks containing appropriate liquid microbiologic media, or in fermenters containing appropriate liquid microbiologic media. Batch fermentation is carried out in sterilized fermentation equipment in volumes ranging from 5 to 2,500 liters. A volume of an overnight culture in LB, Terrific Broth (TB) or similar rich bacteriological medium free of animal derivatives such as bovine albumin of the desired host strain of *Listeria monocytogenes* is incubated with a pre-determined optimal volume of *Listeria monocytogenes* bacteriophage seed stock. Fermentation is carried out at 30° C. to 37° C. for 5-7 h with periodic or continuous monitoring of the $OD_{600}$ until optimal lysis and phage yield for each host-bacteriophage pair has occurred. *Listeria monocytogenes* strains which are lysed by the respective phage may be used for propagation (see Table 2). Each of the 6 *Listeria monocytogenes* bacteriophage has lytic specificity for *Listeria monocytogenes*

ATCC number 35152 (serotype 1/2a), ATTC number 19118 (serotype 4e) and ATCC number 15313 (serotype 1/2a), each of which can be obtained from the ATCC using the ATCC Deposit Accession Number.

TABLE 2

| Phage | Listeria monocytogenes Strains Lysed by Phage |
|---|---|
| List-1 | Lm-4, Lm-26, Lm-54, Lm-91, <u>Lm-107</u>, Lm-171 |
| List-2 | <u>Lm-30</u>, Lm-88, Lm-89, Lm-102, Lm-122, Lm-174 |
| List-3 | Lm-38, Lm-51, Lm-54, Lm-83, Lm-101, Lm-142, <u>Lm-107</u> |
| List-4 | Lm-33, Lm-38, Lm-52, Lm-78, Lm-119, Lm-120, <u>Lm-107</u> |
| List-36 | Lm-27, Lm-90, Lm-101, <u>Lm-117</u>, Lm-140, Lm-155 |
| List-38 | Lm-37, Lm-71, Lm-94, Lm-143, <u>Lm-146</u>, Lm-152 |

The host strains for each phage are underlined.

Bacterial cell suspensions containing phage are cleared of bacteria and bacterial fragments by either low speed centrifugation (usually employed for batches <10 liters), or by tangential flow filtration (usually employed for batches >10 liters). Low speed centrifugation is carried out at 8,000×g for 30 min at 4° C. Supernatant fluids containing *Listeria monocytogenes* bacteriophage are then filtered through an inert 0.45 μm pore size filter, and processed as described below. Instead of centrifugation, larger volumes are:

(1) cleared of bacteria and bacterial debris by tangential flow filtration through 0.22 μM Durapore (Millipore, Inc., Bedford, Mass.) PVDF (or essentially equivalent) filter.

(2) All filtrates are next treated with DNase and RNase, each at concentrations of 0.75 mg/L for 30-60 min at room temperature.

(3) Following nuclease digestion, the bacteriophage are collected, washed, concentrated and exchanged into phosphate-buffered saline by tangential flow filtration using a 100 kDa spiral-wound regenerated cellulose filter (CDUF006LH. Millipore, Inc.)—or essentially equivalent filter. The tangential flow filtration process removes medium components, digested nucleic acids and the nucleases.

(4) The 100 klDa filtration is then followed by filtration through an inert 0.22 μM filter. Batches are handled aseptically following the 0.22 μM filtration.

The concentration of *Listeria monocytogenes* bacteriophage is determined by titration. The concentration of *Listeria monocytogenes* bacteriophage is adjusted to a specific concentration between $10^9$ to $10^{11}$ PFU/ml by dilution with buffer or by concentration by tangential flow filtration. The lytic activity of the final product is then determined by titration. Titrations are highly accurate and reproducible when performed against a single *Listeria monocytogenes* bacterial strain, but not when performed against a mixed culture of strains. The final titer of *Listeria monocytogenes* bacteriophage is calculated.

Following titration, *Listeria monocytogenes* bacteriophage may be freeze-dried or spray-dried after addition of 10% skim milk or similar excipient, or may be maintained and used in liquid form. An appropriate volume of diluent may be added to achieve the specified final working concentration. The required volume can be validated for each lot of *Listeria monocytogenes* bacteriophage by reconstitution of test samples and determination of the lytic titer of the bacteriophage determined as described above.

Example 3

Alternative Production of *Listeria monocytogenes* Bacteriophage Lysate in Liquid Culture Shake flask batches of each phage are produced in 2-L flasks rotated at 100 to 200 rpm in a shaker-incubator (Model C-24; Now Brunswick Scientific Co., Edison, N.J.). *Listeria monocytogenes* strains are grown in Luria-Bertani (LB) broth at 30° C. to an $OD_{600}$ of 0.1-0.3 absorbance units. Cultures are then infected at a multiplicity of infection (MOI; the ratio of phage to bacteria) previously determined to be optimal for each phage. Growth is monitored spectrophotometrically until lysis occurs and the phages are harvested by vacuum filtration (Stericup; Millipore, Billerica, Mass.). The material is then processed as previously described.

Large-scale batches of each phage are generated in a 10-L Bioflo 110 fermenter (New Brunswick Scientific Co., Edison, N.J.) containing 10 L of Terrific Broth (TB) supplemented with 4 ml/L glycerol and Antifoam 204 (Sigma-Aldrich, St. Louis, Mo.) as needed up to a maximum of 200 μl Antifoam 204. The fermenter is inoculated with 100 ml of an actively growing seed culture in TR medium after the $OD_{600}$ of the culture is approximately 1.0 ($1 \times 10^9$ CFU/ml). The fermenter is maintained at a temperature of 30° C., with an aeration rate of 3-7 L/min, a dissolved oxygen level of $\geq 30\%$ and a pH of 7.0±0.1. The pH is controlled by addition of 1.2 N phosphoric acid (cat. no. PX0995-14; EMD Chemicals, Gibbstown, N.J.) or 1 N NaOH (cat. no. VW3225-6; EMD Chemicals, Gibbstown, N.J.), and foaming is controlled by addition of Antifoam 204 as needed up to the previously stated maximum. Cultures are infected at a MOI of 0.01-0.5, based on a cell density of $1 \times 10^8$ CFU/ml at an $OD_{600}$ value of 0.1, when the $OD_{600}$ reaches the desired value. Likewise, infection is terminated when the $OD_{600}$ reaches the desired value. The material is then processed as described previously.

Example 4

Application of *Listeria monocytogenes* Bacteriophage for the Preservation of Food Products

Figure 1B:
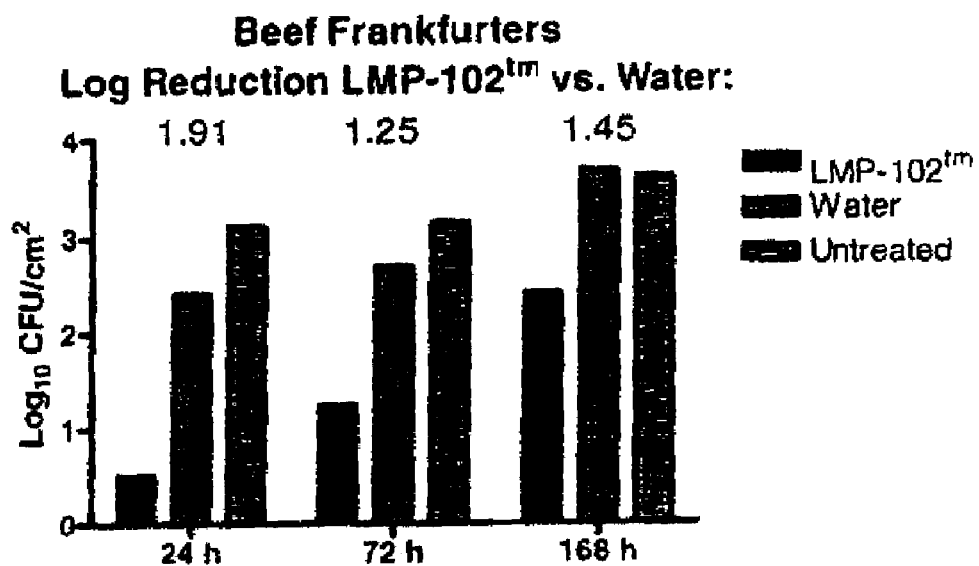
Figure 1C:
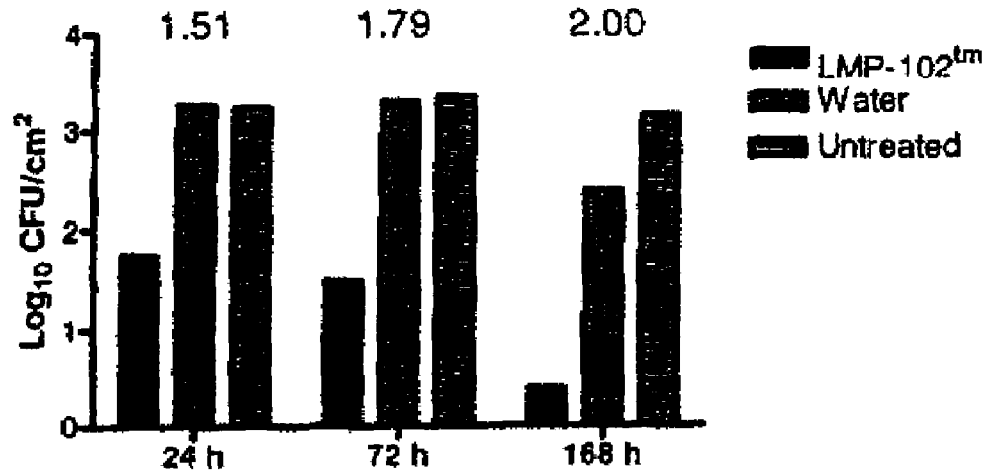
Figure 1D:
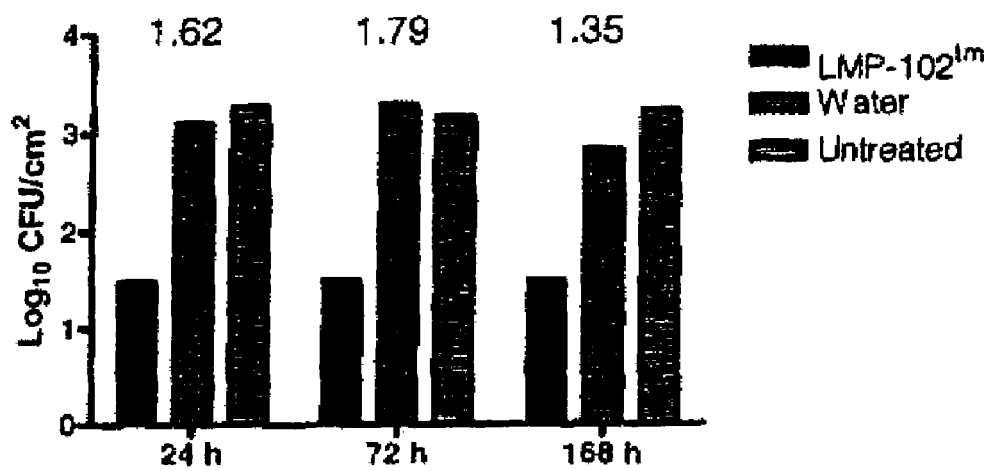
Figure 1E:
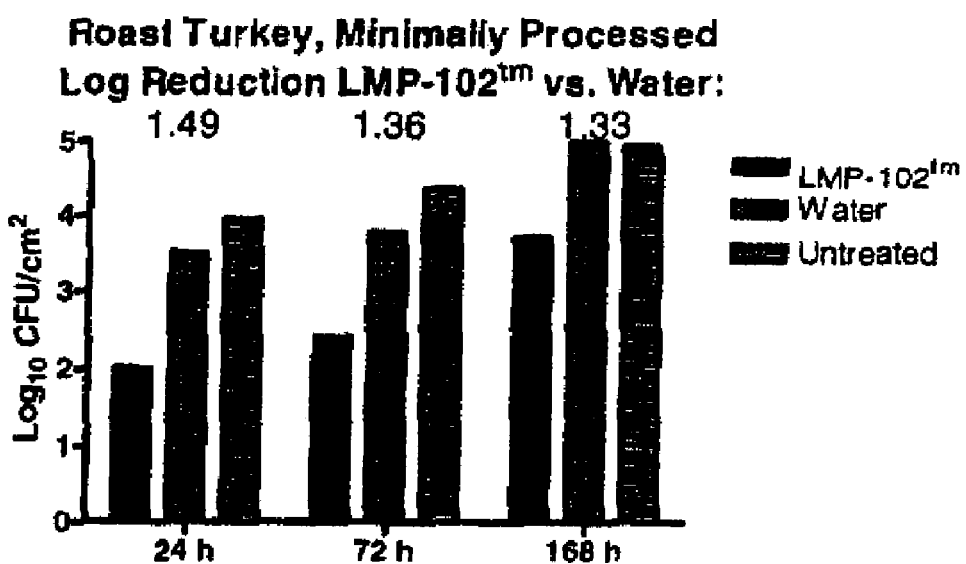
Figure 1F:
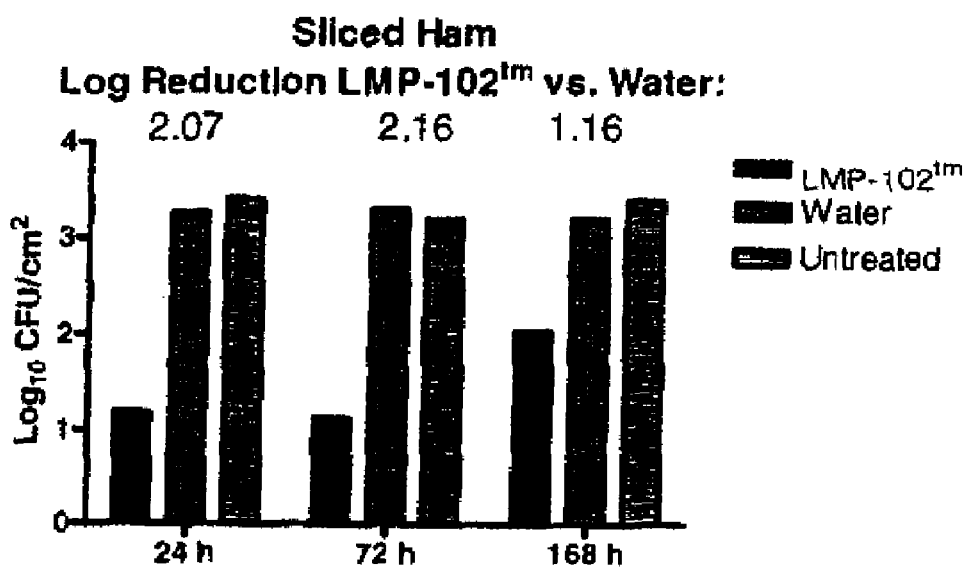
Figure 1G:
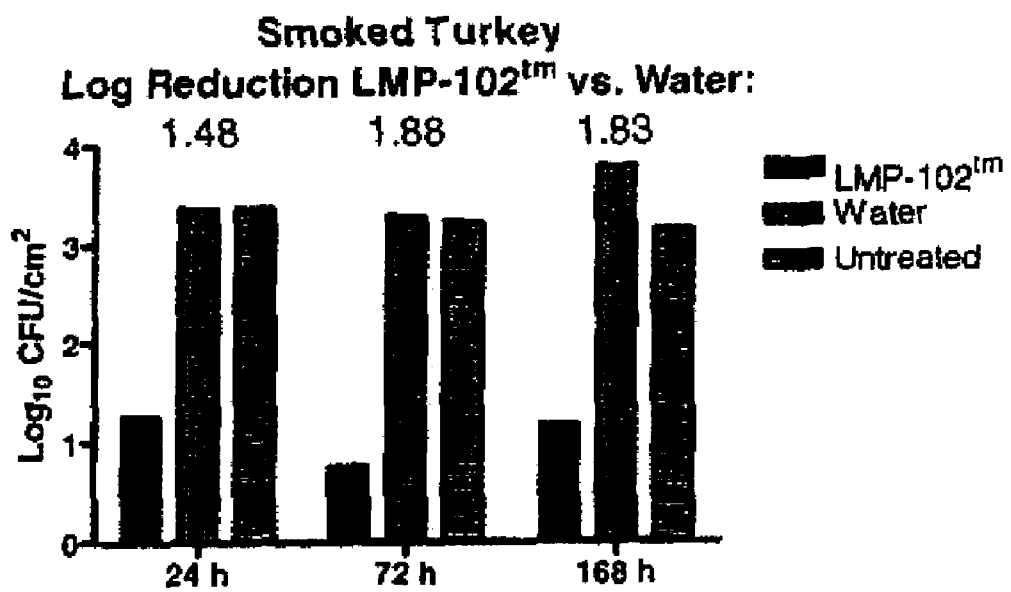
Figure 1H:
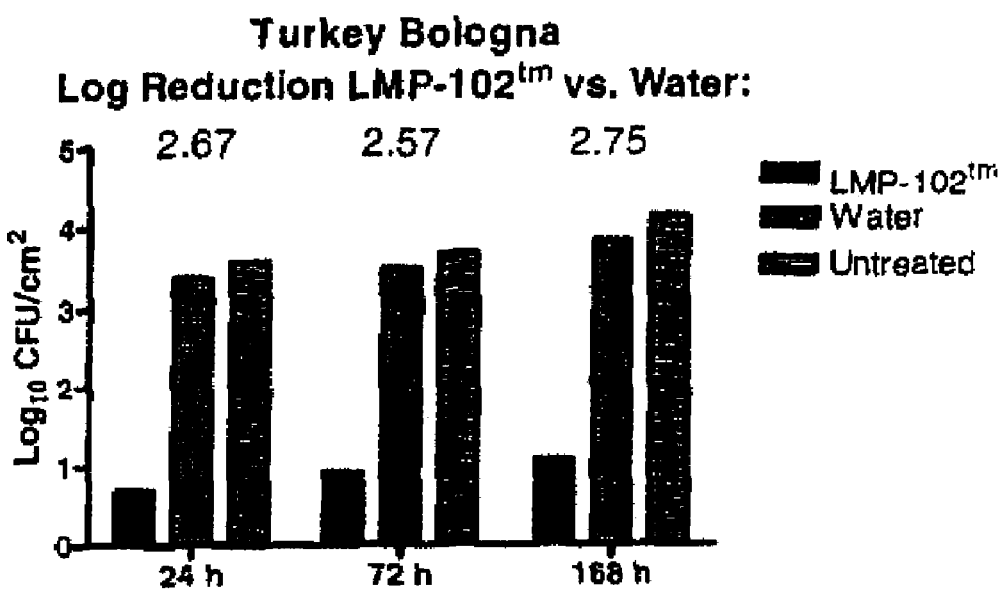
Figure 1I:
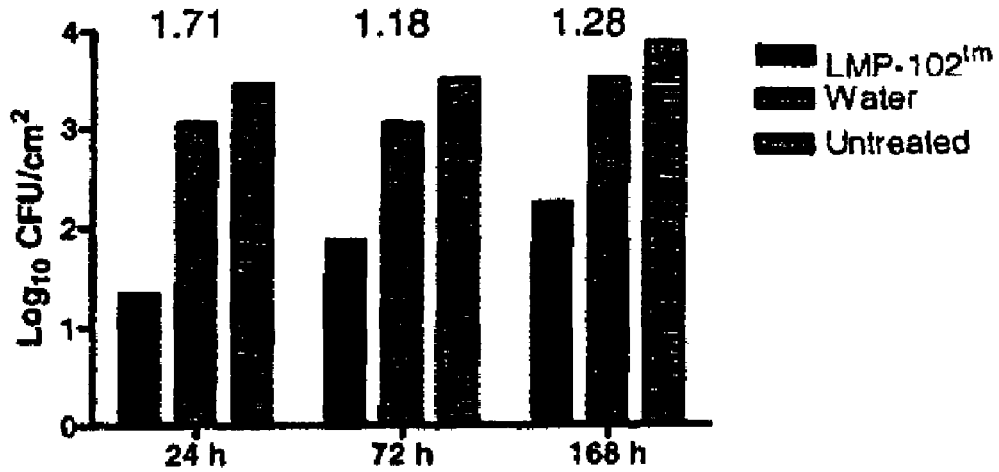
Figure 1J:
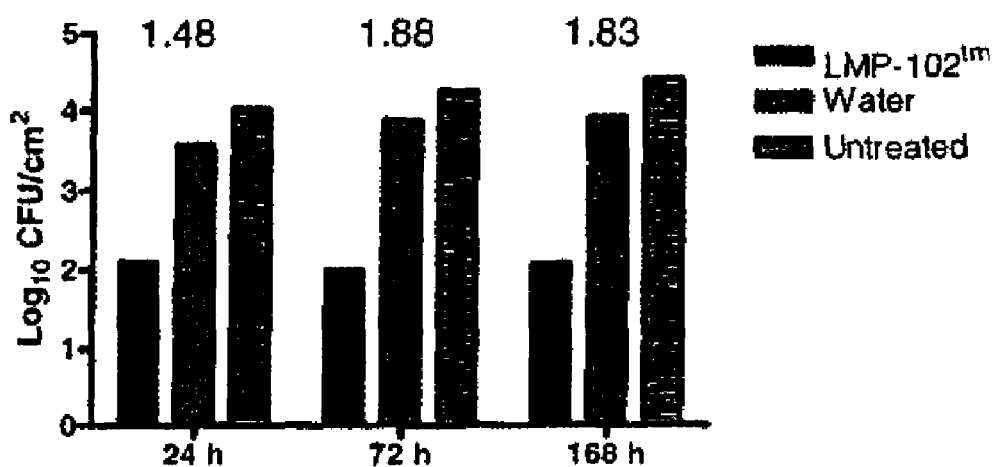
Figure 1K:
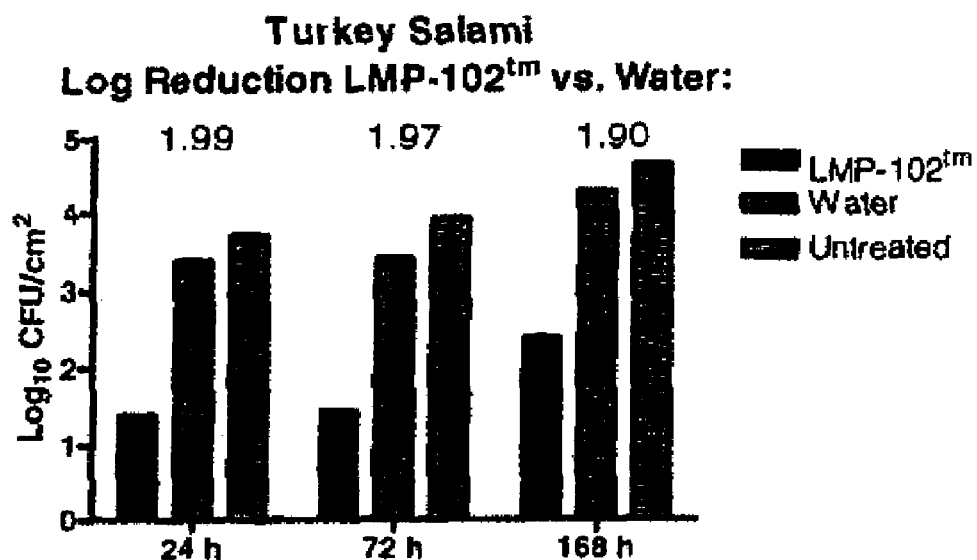
Figure 1L:
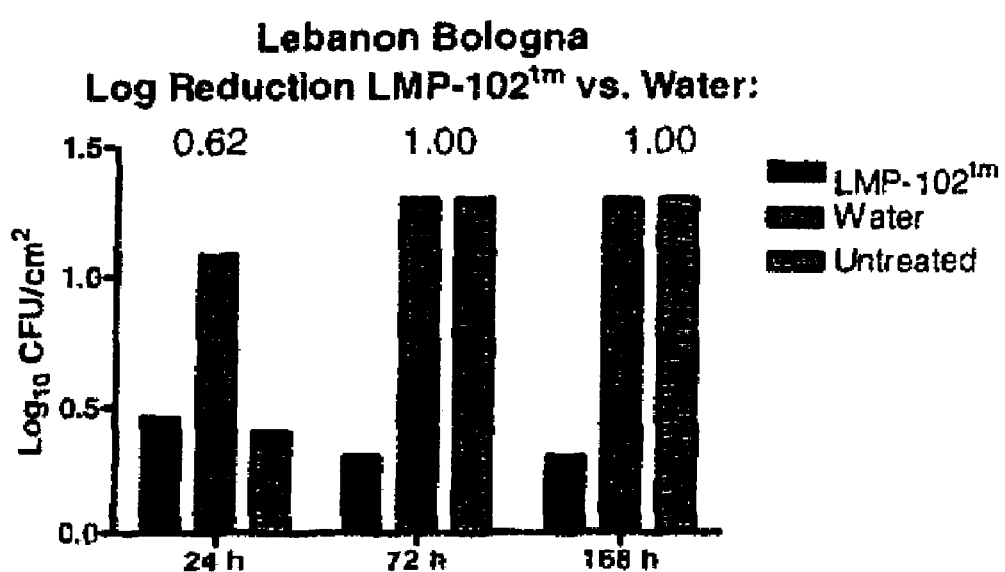

*Listeria monocytogenes* bacteriophage produced using the methods of the present invention may be dispersed in an appropriate aqueous solution or lyophilized or freeze-dried powder and applied to the surface of food products. The data shown in FIGS. 1A-1L show that a mixture of equal parts of the six *Listeria* bacteriophage, List 1, List 2, List 3, List 4, List 36, and List 38, each at $1 \times 10^9$ PFU/ml, achieves reductions of greater than 1 log when applied to the surfaces of ready to eat foodstuffs at a density of 1 ml per 500 cm$^2$. The illustrated foodstuffs were previously contaminated with $2 \times 10^3$ CFU per cm$^2$ of a mixture of equal parts of *Listeria monocytogenes* strains ATCC 19115 (serogroup 4b), Lm 68 (serogroup 1/2b) and Lm 82 (serogroup 1/2a). The food samples were incubated at room temperature for 20 min prior to application of the *Listeria* bacteriophage, and were incubated at 4° C. for the indicated times after the application of phage.

Alternatively, *Listeria monocytogenes* bacteriophage may be included with a cheese culture or other microbially active foodstuff prior to or during processing. The *Listeria monocytogenes* bacteriophage are cultured for a period of time on the surface of the food product or within the food product.

Example 5

Isolation of *Listeria monocytogenes* Bacteriophage DNA

To isolate *Listeria monocytogenes* bacteriophage DNA, 0.75 ml of phage in phosphate-buffered saline solution (at a titer of $10^8$-$10^{11}$ PFU/ml) were collected. To this phage were added 10 μl of proteinase K (20 mg/ml) and 2 μl of RNase (10 mg/ml), followed by incubation at 37° C. for 30 minutes, and a subsequent incubation at 56° C. for 30 minutes. Following incubation, 75 μl of a mixture of 10% SDS (0.1 ml), 0.5 M EDTA (0.1 ml) and 0.8 ml of water were added and incubated at room temperature for 5 min. To that mixture were added 0.75 μl of a phenol:chloroform:isoamyl alcohol (25:24:1) solution, followed by centrifugation at 13,000 rpm for five (5) min.

Next, the supernatant was carefully removed (approximately 600 μl), and transferred to a clean eppendorf tube. Then, 0.6 ml of chloroform were added to the supernatant, mixed well, and centrifuged at 13,000 rpm for five (5) min. The supernatant was then carefully extracted (approximately 500 μl).

Next, 0.1 volume of 3 M sodium acetate (40 ml) was added to the solution, followed by 2.5 volumes of cold 95% ethanol (1 ml) to precipitate the *Listeria monocytogenes* bacteriophage DNA. The solution was allowed to incubate at –20° C. for 1 hour, followed by centrifugation at 13,000 rpm for thirty (30) min.

Following centrifugation, the pellet was washed with 1 ml of 70% cold ethanol, and the supernatant was poured from the pellet. The pellet was allowed to air dry, and was then resuspended in 36-360 μl of TE (10 mM tris-HCL, pH=8.5, 1 mM EDTA).

Example 6

Restriction Fragment Length Polymorphism (RFLP) Profile

DNA was isolated from *Listeria monocytogenes* bacteriophage using Qiagen Plasmid Miniprep or Midiprep kits (Valencia, Calif.) according to the manufacturer's directions. Briefly, the instructions are as follows:

Harvest a desired quantity of *Listeria monocytogenes* bacteriophage by centrifugation at 30,000×g for 2 to 3 h at 4° C. Resuspend the pelleted *Listeria monocytogenes* bacteriophage in 250 μl buffer P1 (10 mM tris-HCl, pH=8, 100 μg/ml RNaseA) and transfer to a microcentrifuge tube. Ensure that 100 μl/ml RNase A has been added to buffer P1. No cell clumps should be visible after resuspension of the pellet. Add 250 μl of buffer P2 (0.2 M NaOH, 2% SDS) and gently invert the tube 4-6 times to mix. Do not vortex, as this will result in shearing of genomic DNA. If necessary, continue inverting the tube until the solution becomes viscous and slightly clear. Do not allow the lysis reaction to proceed for more than 5 min.

Add 350 μl buffer N3 (4.2 M guanidine HCl, 0.9 M potassium acetate, pH=4.8) and invert the tube immediately but gently 4-6 times. To avoid localized precipitation, mix the solution gently but thoroughly, immediately after addition of buffer N3. The solution should become cloudy. Centrifuge for 10 min at maximum speed in a tabletop microcentrifuge. A compact white pellet will form. Apply the supernatant to a plasmid DNA isolation spin column containing silica gel (i.e., "QIAprep® column") by decanting or pipetting. Centrifuge for 30-60 s. Discard the flow-through.

Wash the QIAprep column by adding 0.5 ml buffer PB (5 M guanidine HCl, 30% isopropanol) and centrifuging for 30-60 s. Discard the flow-through. Wash QIAprep column by adding 0.75 ml buffer PE (80% ethanol/water) and centrifuging for 30-60 seconds.

Discard the flow-through to allow for complete removal of the residual wash buffer, and centrifuge for an additional 1 min to remove residual wash buffer. Residual ethanol from buffer PE may inhibit subsequent enzymatic reactions. Place the QIAprep column in a clean 1.5 ml microcentrifuge tube. To elute DNA, add 50 μl buffer EB (10 mM Tris-Cl, pH=8.5) or water to the center of each QIAprep column, let stand for 1 min, and centrifuge for 1 min. Substantially equivalent procedures are followed for isolation of bacteriophage DNA using the larger scale midi-prep kit.

To perform the RFLP experiment with the isolated *Listeria monocytogenes* bacteriophage DNA, the following protocol is followed.

(1) Quantify the DNA by absorbance at 260 nm, and aliquot in a microcentrifuge tube, 0.5-1 μg DNA per *Listeria monocytogenes* bacteriophage sample to be tested. Add, for example, 10 units SpeI and mix, followed by an incubation at 37° C. for 2 hours.

(2) Add tracking dye (bromophenol blue+xylene cyanol) and separate on a 1.0% agarose gel at 80 to 100 V for 50 min. Stain with ethidium bromide. Digestion with one or more additional enzymes (HindIII, and/or EcoRV, and/or EcoRI) may be used if the RFLP patterns using SpeI patterns are identical to provide additional confirmation of identity.

Example 7

Lytic Specificity of *Listeria monocytogenes* bacteriophage

One hundred eighty *L. monocyvogenes* strains were screened for susceptibility to a cocktail consisting of equal parts of LIST-1, LIST-2, LIST-3, LIST-4, LIST-36, and LIST-38 (identified as LMP-102) by the drop on lawn spot test method. Strains were streaked onto LB agar and incubated at 37° C. overnight. Then, 10 μl of the mixture at $10^9$ PFU/ml were dropped in triplicate on the bacterial streak. The plates were incubated for 16 h at 37° C. and evaluated according to the following criteria. If the zone of lysis was less than 1 mm, the result was considered negative. If the zone of lysis was between 1 and 3 mm in diameter with perceptible secondary growth of cells, the *L. monocytogenes* strain was considered moderately susceptible to lysis. If the lysis zone equaled or exceeded 3 mm, the bacterial strain was considered susceptible.

One hundred sixty strains (89%) of *Listeria* were susceptible to LMP-102, a cocktail of the six phage strains of interest, Table 3.

All references cited herein are herein incorporated by reference in entirety.

TABLE 3

Lytic specificity of *Listeria* bacteriophage for various *Listeria* isolates.

| | Internal Lab ID | Serotype | Susceptibility to LMP-102 | Comments |
|---|---|---|---|---|
| 1 | Lm-3 | 1/2a | + | Environmental isolate |
| 2 | Lm-4 | 1/2a | + | Environmental isolate |
| 3 | Lm-5 | 1/2a | + | Environmental isolate |
| 4 | Lm-6 | 1/2a | + | Environmental isolate |

TABLE 3-continued

Lytic specificity of *Listeria* bacteriophage for various *Listeria* isolates.

| | Internal Lab ID | Serotype | Susceptibility to LMP-102 | Comments |
|---|---|---|---|---|
| 5 | Lm-7 | 1/2a | + | Environmental isolate |
| 6 | Lm-8 | 1/2a | + | Environmental isolate |
| 7 | Lm-9 | 1/2a | + | Environmental isolate |
| 8 | Lm-10 | 4b | + | Environmental isolate |
| 9 | Lm-11 | 4a | + | Environmental isolate |
| 10 | Lm-12 | 1/2a | + | Environmental isolate |
| 11 | Lm-13 | 1/2a | + | Environmental isolate |
| 12 | Lm-14 | 1/2a | + | Environmental isolate |
| 13 | Lm-15 | 1/2a | + | Clinical isolate |
| 14 | Lm-17 | 4b | + | Clinical isolate |
| 15 | Lm-18 | 4b | + | Clinical isolate |
| 16 | Lm-19 | 1/2a | + | Clinical isolate |
| 17 | Lm-20 | 1/2a | − | Clinical isolate |
| 18 | Lm-21 | 4b | + | Clinical isolate |
| 19 | Lm-23 | 1/2a | + | Clinical isolate |
| 20 | Lm-24 | 4b | − | Clinical isolate |
| 21 | Lm-25 | 1/2a | − | Clinical isolate |
| 22 | Lm-26 | 1/2a | − | Clinical isolate |
| 23 | Lm-27 | 1/2a | + | Environmental isolate |
| 24 | Lm-28 | 1/2a | − | Environmental isolate |
| 25 | Lm-29 | 4a | + | Environmental isolate |
| 26 | Lm-30 | ND | + | Host strain for List-2 phage; environmental isolate |
| 27 | Lm-32 | 4b | + | Environmental isolate |
| 28 | Lm-33 | 1/2a | + | Environmental isolate |
| 29 | Lm-34 | 1/2a | − | Environmental isolate |
| 30 | Lm-35 | NT | + | Environmental isolate |
| 31 | Lm-37 | 4a | + | Clinical isolate |
| 32 | Lm-38 | 1/2a | + | Environmental isolate |
| 33 | Lm-39 | 1/2a | + | Environmental isolate |
| 34 | Lm-40 | 1/2a | + | Environmental isolate |
| 35 | Lm-42 | 1/2a | − | Environmental isolate |
| 36 | Lm-43 | 1/2a | + | Environmental isolate |
| 37 | Lm-45 | 1/2a | − | Environmental isolate |
| 38 | Lm-46 | 4b | + | Environmental isolate |
| 39 | Lm-49 | NT | + | Environmental isolate |
| 40 | Lm-50 | 1/2a | + | Environmental isolate |
| 41 | Lm-51 | 4b | + | Clinical isolate |
| 42 | Lm-52 | 4b | − | Clinical isolate |
| 43 | Lm-53 | 1/2a | + | Clinical isolate |
| 44 | Lm-54 | 1/2a | + | Clinical isolate |
| 45 | Lm-55 | 1/2a | + | Clinical isolate |
| 46 | Lm-56 | 1/2a | + | Clinical isolate |
| 47 | Lm-57 | 3b | − | Clinical isolate |
| 48 | Lm-59 | 1/2a | + | Clinical isolate |
| 49 | Lm-61 | 1/2b | − | Clinical isolate |
| 50 | Lm-62 | 1/2a | + | Clinical isolate |
| 51 | Lm-63 | 1/2b | + | Clinical isolate |
| 52 | Lm-64 | 3b | + | Clinical isolate |
| 53 | Lm-65 | 1/2b | + | Clinical isolate |
| 54 | Lm-66 | 1/2b | + | Clinical isolate |
| 55 | Lm-67 | 1/2b | + | Clinical isolate |
| 56 | Lm-68 | 1/2b | + | Clinical isolate |
| 57 | Lm-69 | 1/2a | + | Clinical isolate |
| 58 | Lm-70 | 1/2a | + | Clinical isolate |
| 59 | Lm-71 | 1/2a | + | Clinical isolate |
| 60 | Lm-72 | 4d | + | Clinical isolate |
| 61 | Lm-73 | 1/2b | + | Clinical isolate |
| 62 | Lm-74 | 1/2b | + | Clinical isolate |
| 63 | Lm-75 | 1/2b | − | Clinical isolate |
| 64 | Lm-76 | 1/2b | + | Clinical isolate |
| 65 | Lm-77 | 4b | + | Clinical isolate |
| 66 | Lm-78 | 4b | + | Clinical isolate |
| 67 | Lm-79 | 1/2a | + | Clinical isolate |
| 68 | Lm-80 | 1/2a | ± | Clinical isolate |
| 69 | Lm-81 | 4b | + | Clinical isolate |
| 70 | Lm-82 | 1/2a | + | CDC standard strain H2446; clinical isolate |
| 71 | Lm-83 | 1/2b | + | Clinical isolate |
| 72 | Lm-84 | 1/2b | + | Clinical isolate |
| 73 | Lm-85 | 4b | + | Clinical isolate |
| 74 | Lm-86 | 1/2b | + | Clinical isolate |
| 75 | Lm-87 | 1/2a | + | Clinical isolate |
| 76 | Lm-88 | 4a | ± | Clinical isolate |
| 77 | Lm-89 | NT | + | Clinical isolate |
| 78 | Lm-90 | 4b | + | Clinical isolate |
| 79 | Lm-91 | 1/2a | + | Clinical isolate |
| 80 | Lm-92 | 1/2a | − | Clinical isolate |
| 81 | Lm-93 | 1/2a | + | Clinical isolate |
| 82 | Lm-94 | 4b | − | Clinical isolate |
| 83 | Lm-95 | 1/2a | + | Clinical isolate |
| 84 | Lm-96 | 4b | + | Environmental isolate |
| 85 | Lm-97 | 1/2a | + | Clinical isolate |
| 86 | Lm-98 | 1/2a | + | Clinical isolate |
| 87 | Lm-99 | 4b | + | Clinical isolate |
| 88 | Lm-100 | 1/2c | + | Clinical isolate |
| 89 | Lm-101 | 1/2c | + | Clinical isolate |
| 90 | Lm-102 | ND | + | Clinical isolate |
| 91 | Lm-103 | 4b | + | Clinical isolate |
| 92 | Lm-104 | 4b | + | Clinical isolate |
| 93 | Lm-105 | 1/2a | + | Clinical isolate |
| 94 | Lm-106 | 1/2a | + | Clinical isolate |
| 95 | Lm-107 | 1/2a | + | Host strain for List-1, List-3 and List-4 phages; clinical isolate |
| 96 | Lm-108 | 4b | + | Clinical isolate |
| 97 | Lm-109 | 1/2c | + | Clinical isolate |
| 98 | Lm-110 | 1/2a | + | Clinical isolate |
| 99 | Lm-111 | 1/2a | + | Clinical isolate |
| 100 | Lm-112 | 1/2c | + | Clinical isolate |
| 101 | Lm-113 | 1/2a | + | Clinical isolate |
| 102 | Lm-114 | 4b | + | Environmental isolate |
| 103 | Lm-115 | 4b | + | Clinical isolate |
| 104 | Lm-116 | 4b | + | Clinical isolate |
| 105 | Lm-117 | 4b | + | Host strain for List-36 phage; clinical isolate |
| 106 | Lm-118 | 4b | + | Clinical isolate |
| 107 | Lm-119 | 1/2a | + | Environmental isolate |
| 108 | Lm-120 | 4b | + | Environmental isolate |
| 109 | Lm-121 | 1/2a | + | Environmental isolate |
| 110 | Lm-122 | 1/2a | + | Environmental isolate |
| 111 | Lm-123 | 1/2a | + | Environmental isolate |
| 112 | Lm-124 | NT | + | Environmental isolate |
| 113 | Lm-125 | 4b | + | Environmental isolate |
| 114 | Lm-126 | 1/2b | + | Environmental isolate |
| 115 | Lm-127 | 1/2a | + | Environmental isolate |
| 116 | Lm-128 | 1/2b | + | Environmental isolate |
| 117 | Lm-129 | 1/2a | + | Environmental isolate |
| 118 | Lm-130 | 1/2a | + | Environmental isolate |
| 119 | Lm-131 | 1/2a | + | Clinical isolate |
| 120 | Lm-132 | 1/2b | ± | Clinical isolate |
| 121 | Lm-133 | NT | + | Clinical isolate |
| 122 | Lm-134 | NT | + | Clinical isolate |
| 123 | Lm-135 | 1/2a | + | Clinical isolate |
| 124 | Lm-136 | 1/2a | + | Clinical isolate |
| 125 | Lm-137 | 1/2a | + | Clinical isolate |
| 126 | Lm-138 | NT | + | Clinical isolate |
| 127 | Lm-139 | 1/2a | + | Clinical isolate |
| 128 | Lm-140 | 1/2a | + | Clinical isolate |
| 129 | Lm-141 | 1/2a | + | Clinical isolate |
| 130 | Lm-142 | 1/2a | + | Environmental isolate |
| 131 | Lm-143 | 1/2b | + | Environmental isolate |
| 132 | Lm-144 | 4b | + | Environmental isolate |
| 133 | Lm-145 | 1/2a | + | Environmental isolate |
| 134 | Lm-146 | 1/2a | + | Host strain for List-38 phage; environmental isolate |
| 135 | Lm-147 | 1/2a | + | Environmental isolate |
| 136 | Lm-148 | 1/2a | − | Environmental isolate |
| 137 | Lm-149 | 1/2a | − | Environmental isolate |
| 138 | Lm-150 | 1/2a | + | Environmental isolate |
| 139 | Lm-151 | 1/2a | + | Environmental isolate |
| 140 | Lm-152 | ND | + | Environmental isolate |
| 141 | Lm-153 | 1/2a | + | Environmental isolate |
| 142 | Lm-154 | 1/2a | + | Environmental isolate |
| 143 | Lm-155 | 1/2a | + | Environmental isolate |
| 144 | Lm-156 | 1/2a | + | Environmental isolate |

TABLE 3-continued

Lytic specificity of *Listeria* bacteriophage for various *Listeria* isolates.

| | Internal Lab ID | Serotype | Susceptibility to LMP-102 | Comments |
|---|---|---|---|---|
| 145 | Lm-157 | 1/2a | + | Environmental isolate |
| 146 | Lm-158 | 1/2a | + | Environmental isolate |
| 147 | Lm-159 | 4a | + | Environmental isolate |
| 148 | Lm-160 | 1/2a | + | Environmental isolate |
| 149 | Lm-161 | 1/2a | + | Environmental isolate |
| 150 | Lm-162 | 1/2a | + | Environmental isolate |
| 151 | Lm-163 | 1/2a | + | Environmental isolate |
| 152 | Lm-164 | 1/2a | + | Environmental isolate |
| 153 | Lm-165 | 1/2a | + | Clinical isolate |
| 154 | Lm-166 | 1/2a | + | Clinical isolate |
| 155 | Lm-167 | 4b | + | Clinical isolate |
| 156 | Lm-168 | 4b | + | Clinical isolate |
| 157 | Lm-169 | 1/2a | + | Clinical isolate |
| 158 | Lm-170 | 1/2a | + | Clinical isolate |
| 159 | Lm-171 | 1/2b | + | Clinical isolate |
| 160 | Lm-172 | 1/2a | + | Clinical isolate |
| 161 | Lm-174 | 1/2a | + | Environmental isolate |
| 162 | Lm-175 | 1/2a | + | Environmental isolate |
| 163 | Lm-176 | NT | − | Environmental isolate |
| 164 | Lm-177 | 4b | + | Environmental isolate |
| 165 | Lm-178 | 4b | + | Clinical isolate |
| 166 | Lm-183 | NT | + | Environmental isolate |
| 167 | Lm-184 | 1/2a | + | Environmental isolate |
| 168 | Lm-185 | NT | + | Environmental isolate |
| 169 | Lm-191 | 1/2a | + | Environmental isolate |
| 170 | Lm-192 | 1/2a | − | Environmental isolate |
| 171 | Lm-193 | 3a | + | Unknown |
| 172 | Lm-194 | NT | + | Unknown |
| 173 | Lm-195 | 1/2a | + | Unknown |
| 174 | Lm-196 | 1/2a | + | Unknown |
| 175 | Lm-198 | 1/2a | + | Unknown |
| 176 | Lm-200 | 1/2b | − | Unknown |
| 177 | Lm-201 | 1/2b | + | Unknown |
| 178 | Lm-300 | 1/2c | + | Environmental isolate |
| 179 | Lm-301 | 1/2a | + | Environmental isolate |
| 180 | Lm-302 | 4b | + | Environmental isolate |

Clinical isolate designates an isolate from a patient with listeriosis, or from an asymptomatic carrier
NA = not available, PFGE typing performed, but PFGE type not yet assigned
NT = Not Typeable
+ Lysis zone ≧3 mm, clear of secondary colonies
± Lysis zone 1-3 mm, with some visually detectable secondary growth of cells
− Lysis zone ≦3 mm The table may be summarized as follows:
17 (9.4%) strains are resistant to LMP-102™
3 (1.7%) strains are moderately susceptible to LMP-102™
160 (88.9%) strains are susceptible to LMP-102™

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. An isolated bacteriophage of a bacteriophage strain selected from the group consisting of List-1, List-2, List-3, List-4, List-36, and List-38 deposited under ATCC Accession Nos. PTA-5372, PTA-5373, PTA-5374, PTA-5375, PTA-5376, and PTA-377, respectively, and variants thereof, wherein said variants retain the phenotypic characteristics of said deposited phage, and wherein said bacteriophage, and variants thereof, have lytic activity against *Listeria monocytogenes* strains.

2. A composition comprising at least two of said bacteriophage strains of claim 1.

3. A composition comprising at least three of said bacteriophage strains of claim 1.

4. A composition comprising at least four of said bacteriophage strains of claim 1.

5. A composition comprising at least five of said bacteriophage strains of claim 1.

6. A composition comprising at least six of said bacteriophage strains of claim 1.

7. An isolated bacteriophage of a bacteriophage strain selected from the group consisting of List-1, List-2, List-4, List-36, and List-38 deposited under ATCC Accession Nos. PTA-5372, PTA-5373, PTA-5375, PTA-5376, and PTA-5377, respectively, and variants thereof, wherein said variants retain the phenotypic characteristics of said deposited phage, and wherein said bacteriophage, and variants thereof, have lytic activity against *Listeria monocytogenes* strains.

* * * * *

UNITED STATES PATENT AND TRADEMARK OFFICE
CERTIFICATE OF CORRECTION

PATENT NO. : 7,507,571 B2  Page 1 of 1
APPLICATION NO. : 11/764587
DATED : March 24, 2009
INVENTOR(S) : Gary R. Pasternack It is certified that error appears in the above-identified patent and that said Letters Patent is hereby corrected as shown below:

Col. 24, Claim 1, line 20, please change "PTA-377" to --PTA-5377--.

Signed and Sealed this

Fifteenth Day of June, 2010

David J. Kappos
*Director of the United States Patent and Trademark Office*